(12) United States Patent
Kassab et al.

(10) Patent No.: US 8,216,271 B2
(45) Date of Patent: Jul. 10, 2012

(54) DEVICES, SYSTEMS, AND METHODS FOR ENDOSCOPIC GASTRIC MAGNETIC RESTRICTION

(75) Inventors: Ghassan S. Kassab, Zionsville, IN (US); Jose A. Navia, Sr., Buenos Aires (AR)

(73) Assignee: CVDevices, LLC, Zionzville, IN (US)

( * ) Notice: Subject to any disclaimer, the term of this patent is extended or adjusted under 35 U.S.C. 154(b) by 404 days.

(21) Appl. No.: 12/522,700

(22) PCT Filed: Jan. 23, 2008

(86) PCT No.: PCT/US2008/000837
§ 371 (c)(1),
(2), (4) Date: Jul. 9, 2009

(87) PCT Pub. No.: WO2008/147476
PCT Pub. Date: Dec. 4, 2008

(65) Prior Publication Data
US 2010/0106185 A1    Apr. 29, 2010

Related U.S. Application Data

(60) Provisional application No. 60/881,838, filed on Jan. 23, 2007.

(51) Int. Cl.
*A61B 17/08* (2006.01)
(52) U.S. Cl. ....................................................... 606/213
(58) Field of Classification Search .................. 606/153, 606/213, 215; 128/898; 600/9, 12; 604/8
See application file for complete search history.

(56) References Cited

U.S. PATENT DOCUMENTS

| | | | |
|---|---|---|---|
| 4,648,383 A | | 3/1987 | Angelchik |
| 5,088,979 A | * | 2/1992 | Filipi et al. ................... 604/26 |
| 5,306,300 A | | 4/1994 | Berry |
| 5,860,426 A | | 1/1999 | Kleiman |
| 5,910,149 A | | 6/1999 | Kuzmak |
| 6,675,809 B2 | | 1/2004 | Stack et al. |
| 7,090,699 B2 | | 8/2006 | Geitz |
| 7,175,669 B2 | | 2/2007 | Geitz |
| 7,220,237 B2 | | 5/2007 | Gannoe et al. |
| 7,267,694 B2 | | 9/2007 | Levine et al. |
| 2001/0054425 A1 | | 12/2001 | Bertram |
| 2002/0068946 A1 | | 6/2002 | Kortenbach et al. |
| 2002/0082621 A1 | * | 6/2002 | Schurr et al. ................. 606/151 |
| 2002/0086842 A1 | | 7/2002 | Plank et al. |

(Continued)

FOREIGN PATENT DOCUMENTS

WO    WO/2005/084287    9/2005

(Continued)

OTHER PUBLICATIONS

PCT/US2008/000837, International Searching Authority, PCT Search Report and Written Opinion, dated Jul. 7, 2008.

*Primary Examiner* — Melanie Tyson
*Assistant Examiner* — Son Dang
(74) *Attorney, Agent, or Firm* — Ice Miller LLP

(57) ABSTRACT

A device, system and method for providing tissue and organ restriction. A device is described with respect to restricting gastric capacity while avoiding nutritional deficiencies and other complications. Additionally, a system and method are described for using the device to restrict gastric capacity to perform a non surgical gastric procedure.

34 Claims, 12 Drawing Sheets

U.S. PATENT DOCUMENTS

| | | |
|---|---|---|
| 2003/0191476 A1 | 10/2003 | Smit |
| 2004/0064098 A1 | 4/2004 | Cuschieri et al. |
| 2004/0176788 A1 | 9/2004 | Opolski |
| 2004/0267291 A1 | 12/2004 | Byrum et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0096750 A1 | 5/2005 | Kagan et al. |
| 2005/0197714 A1 | 9/2005 | Sayet |
| 2005/0261568 A1 | 11/2005 | Hular et al. |
| 2005/0273060 A1 | 12/2005 | Levy et al. |
| 2006/0093641 A1 | 5/2006 | Bates |
| 2006/0122462 A1 | 6/2006 | Roth et al. |
| 2006/0178691 A1 | 8/2006 | Binmoeller |
| 2007/0118159 A1* | 5/2007 | Deem et al. .......... 606/153 |
| 2007/0239284 A1 | 10/2007 | Skerven et al. |

FOREIGN PATENT DOCUMENTS

| | | |
|---|---|---|
| WO | WO/2005/110280 | 11/2005 |
| WO | WO/2006/110565 | 10/2006 |
| WO | WO/2006/133311 | 12/2006 |
| WO | WO/2006/135297 | 12/2006 |
| WO | WO/2007/139920 | 12/2007 |
| WO | WO/2007/142829 | 12/2007 |
| WO | WO/2007/142834 | 12/2007 |

* cited by examiner

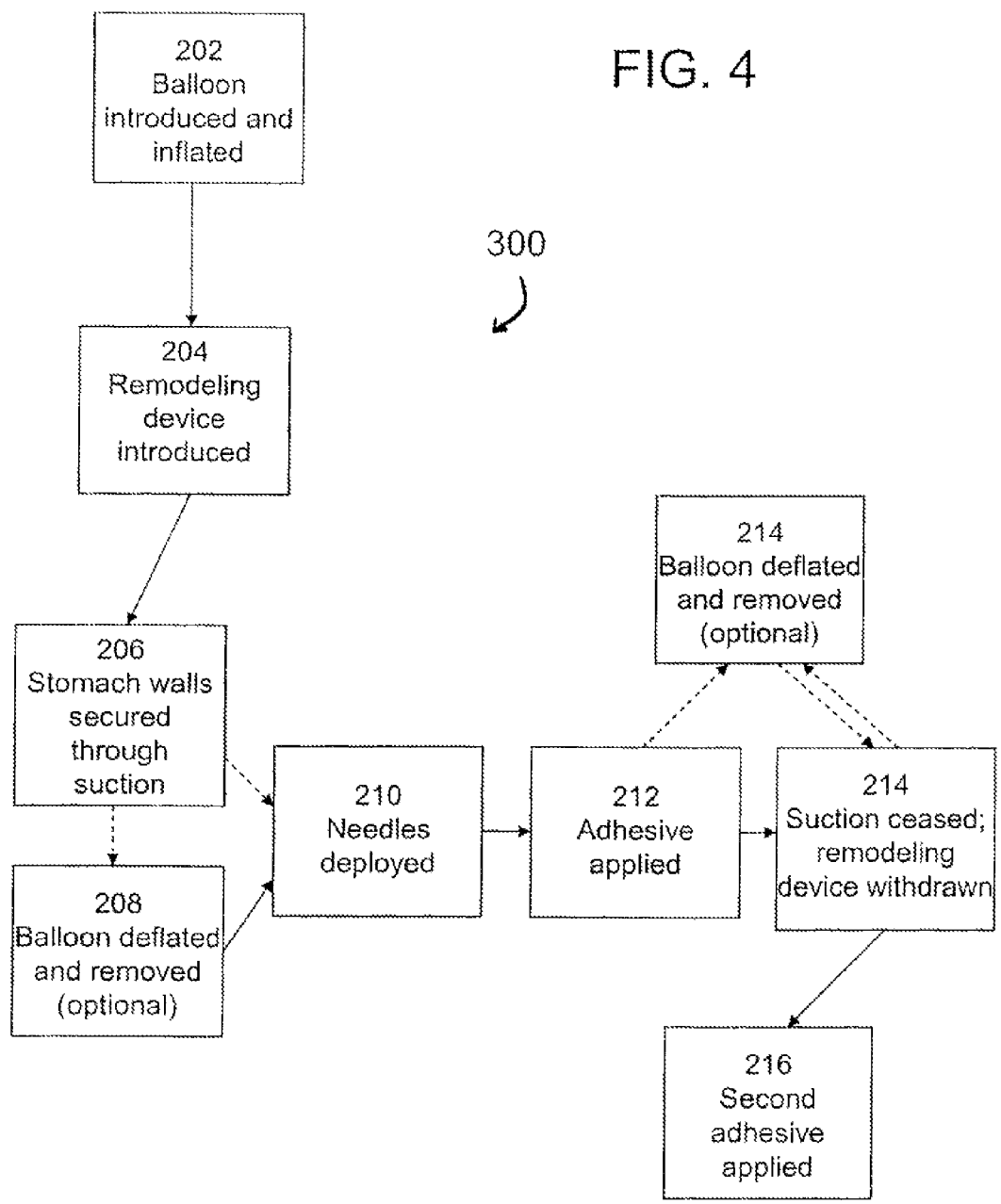

DEVICES, SYSTEMS, AND METHODS FOR ENDOSCOPIC GASTRIC MAGNETIC RESTRICTION

PRIORITY

The present application is related to, and claims the priority benefit of, International Patent Application Serial No. PCT/US2008/000837, filed Jan. 23, 2008, which: (1) is related to, and claims the priority benefit of, U.S. Provisional Patent Application Ser. No. 60/881,838, filed Jan. 23, 2007; and (2) is related to, and claims the priority benefit of, International Patent Application Ser. No. PCT/US2007/015238, filed Jun. 29, 2007, which is related to, and claims the priority benefit of, U.S. Provisional Patent Application Serial No. 60/817,423, filed Jun. 30, 2006. The contents of each of these applications are hereby incorporated by reference in their entirety into this disclosure.

BACKGROUND

Obesity and overweight conditions are a global epidemic and are the most frequent nutritional disorder in Western civilization. Currently, the conditions of "overweight" and "obesity" are classified by body mass index ("BMI"), which is a statistical measure of the weight of a person scaled according to height. From the period of 1988-1994 to the period of 1999-2000, the incidence of overweight adults augmented from 55.9% to 64.5% while the prevalence of obesity increased from 22.9% to 30.5%. The United States especially faces grave public policy concerns with respect to the morbidly obese, i.e. being over 100 pounds above their desirable weight or having one or more serious medical conditions in association with obesity.

In order to treat obesity, conventional procedures involve attempts to either 1) restrict food intake into the body via a restrictive bariatric procedure (a "Restrictive Procedure"), or 2) alter the anatomy of the small intestine or divert the peristalsis of a person's normal food intake past the small intestine to decrease caloric absorption via a malabsorptive bariatric procedure, which is commonly known as a gastric bypass (a "Malabsorptive Procedure"). It is also known to combine the two procedures such that both of the aforementioned techniques are employed jointly.

Each of the abovementioned procedures has advantages and disadvantages. The Malabsorptive Procedures, which entail short circuiting the gastric pouch, have previously been more successful in bringing about sustained weight loss; however, they are typically more difficult to perform, have higher rates of catastrophic post-operative complications, and produce long-term deleterious changes due to the rerouting of the alimentary flow. Restrictive Procedures have encountered more success than Malabsorptive Procedures because the Restrictive Procedures tend to be simpler, have fewer major complications, and do not disturb normal digestive tract continuity.

In Malabsorptive Procedures, an intestinal bypass is typically performed. This results in the exclusion of almost all of the small intestine from the digestive tract, such that a lower amount of calories and nutrients can be absorbed. One example of a specific Malabsorptive Procedure is the biliopancreatic diversion ("BPD"). BPD is a procedure in which about three-fourths (¾) of the stomach is removed in order to restrict food intake and decrease stomach acid production. The effect of this procedure is to alter the anatomy of the small intestine via the formation of an alimentary limb. The alimentary limb diverts the passage of food past the first portion of the small intestine, including the duodenum and jejunum, thereby preventing all of the bile and pancreatic juices from digesting the ingested food. As briefly noted above, this process does not come without significant risks.

Conversely, in Restrictive Procedures a passageway is generally constructed from the upper portion of the stomach to the lower portion, thereby preventing the stomach from storing large amounts of food and slowing the passage of food from the esophagus to the small intestine. Conventional Restrictive Procedures rely on the banding and/or stapling of the stomach to create a small pouch on the superior portion of the stomach near the gastroesophageal junction. When first created, this pouch can contain no more than approximately one (1) ounce of food and liquid, but typically later distends to store two (2) to three (3) ounces.

The lower outlet of the created pouch is nondilatable and is typically only one half (½) inch in diameter or smaller. The small pouch receives food and liquid directly from the esophagus and fills quickly. The pouch also diverts the passage of food and liquid to the lower portion of the stomach, thus avoiding storage of food in the stomach itself. Due to the pouch's size and the relatively narrow outlet into the larger stomach, the patient experiences early satiety, which in turn decreases appetite and results in weight loss. Purely Restrictive Procedures for obesity include adjustable gastric banding and vertical banded gastroplasty. These procedures do not affect the digestive process and thus do not result in the risks associated with Malabsorptive Procedures. In addition, Restrictive Procedures are safer than Malabsorptive Procedures and can be performed laparoscopically, thereby further reducing risks of complications.

In all Restrictive Procedures, the volume of the small pouch above the band can increase in size up to ten (10) times after the initial operation. Therefore, the pouch volume during surgery needs to initially be very small. To enable the patient to consume sufficient nutrition immediately after the operation considering such a small gastric pouch 11, the opening to the stomach initially must be relatively large. Thereafter, as the pouch volume increases, the stoma opening must be subsequently reduced to enjoy optimal results of the procedure. In addition, the size of the stoma opening should be gradually reduced during the first year after surgery as the gastric pouch continues to increase in size.

One Restrictive Procedure, adjustable gastric binding ("AGB"), provides an adjustment means, thereby enabling minor post-operation adjustments of the size of the stoma opening. In AGB, a band is placed around the superior portion of the stomach to form a small pouch and a narrow passageway to the rest of the stomach. The band itself typically comprises a hollow silicone rubber band having an inflatable cavity. The inflatable cavity of the band is capable of being inflated with a fluid—typically an isotonic salt solution—through a tube that connects the band to an access port, which is typically located subcutaneously so that it may be easily accessed by the patient. Over time, the band may be tightened or loosened to modify the size of the stoma opening by increasing or decreasing the quantity of fluid within the cavity of the band. By adding liquid to the cavity of the band, the band expands radially inward and decreases the size of the stoma opening.

A great disadvantage of AGB, however, is that as a result of the direct manipulation of the bands, the rubber bands forming the gastric pouch tend to slip or wear away. In addition, in the conventional AGB process where the fluid is added to the band cavity by way of an injection into the access port, repeated injections into the same area increases the risk of infection in the area surrounding the access port. In addition, it is uncomfortable for the patient when the necessary post-operation adjustments of the stoma opening are carried out by using a needle to access the port through the skin.

Similar to AGB, vertical banded gastroplasty ("VBG") is a Restrictive Procedure that utilizes rubber bands as well as staples to create the small stomach pouch. Unlike AGB, however, VBG is not manually adjustable. The VBG procedure involves puncturing the stomach to create a pouch. Like AGB, VBG is prone to slippage and/or band deterioration. Additional complications also may arise with VBG, including staple-line disruption, which can result in stomach content leakage and/or serious infection. Such complications may require prolonged hospitalization with antibiotic treatment and even additional operations. Based on the associated risks, VBG has been classified by the American Medical Association as a "severely dangerous" operation.

Combined operations consisting of Malabsorptive and Restrictive Procedures are the most common bariatric procedures performed today. Such combined procedures restrict both food intake and the amount of calories and nutrients that the body is capable of absorbing. An example of a combined procedure is the Extended (Distal) Roux-en-Y Gastric Bypass ("RYGBP-E") in which a stapling creates a small (approximately 15 to 20 cc) stomach pouch completely separated from the remainder of the stomach. The small intestine is divided just beyond the duodenum (the hollow tube connecting the stomach to the jejunum), and is re-arranged into a Y-configuration to enable outflow of food from the small upper stomach pouch, via a "Roux limb". Accordingly, the small intestine forms the outlet of the newly formed stomach pouch, which empties directly into the lower portion of the jejunum, thus bypassing caloric absorption. The length of either segment of the intestine can be increased to adjust the levels of malabsorption.

Because the duodenum is bypassed in this procedure, poor absorption of iron and calcium can result in a decreased total body iron concentration and a predisposition to iron deficiency anemia. Additional complications of the RYGBP-E procedure include a condition known as "dumping syndrome". Normally, the pyloric valve at the lower end of the stomach regulates the release of food into the bowel. Dumping syndrome is a condition in which the stomach contents rapidly pass into the small intestine resulting in extremely unpleasant conditions including nausea, weakness, sweating, faintness and, on occasion, diarrhea after eating. Because sugar passes especially rapidly into the bowel, some patients are unable to eat any form of sweets after RYGBP-E surgery.

Being obese has many health ramifications. Obesity is an important risk factor for a number of diseases and increases risk factors that heavily predispose for cardiovascular disease. In addition, systemic hypertension, pulmonary hypertension (left ventricular failure, chronic hypoxia), and coronary heart disease all occur at very high rights in obese individuals and may be the source or influence in cardiac structure and function alterations. The risk of sudden cardiac death is also elevated in obese individuals.

Accordingly, a need exists for a safe and effective method of treating obesity. The current Restrictive, Malabsorptive, and combination procedures present a high risk of several complications, including malnutrition, infections, vomiting, and recurrence resulting from band slippage or deterioration. There is therefore a need for a new restrictive, nonsurgical technique that is not subject to the complications associated with the conventional procedures known in the art.

SUMMARY

Devices, systems and methods are provided for the treatment of obesity and, specifically, for restricting the medically effective volume of a stomach. In one embodiment, the device comprises a probe comprising at least one lumen and a plurality of openings therein, a puncturing device for insertion within the at least one lumen of the probe, and a vacuum source. Embodiments of the device can be endoscopically placed within the stomach and operated to create two stomach portions. The first portion of the stomach is for the primary digestion of ingested food, while the second portion of the stomach is bypassed in the digestive process.

In additional embodiments, a device is provided for restricting the capacity of a stomach and forming a gastric evacuation channel. The device comprises a double-lumen probe having a plurality of openings and a plurality of suction ports, a vacuum source, and a component comprising a plurality of retractable needles. The component comprising the plurality of retractable needles may further include a sheath configured to encase the component such that the retractable needles will be retracted therein and shielded from surrounding tissue or organs. In one embodiment, the component is further configured to be slidably inserted within the lumen of the probe operatively connected with the plurality of openings and the vacuum source is configured to be coupled with the lumen of the probe operatively connected to the plurality of suction ports. In this manner, suctional force provided through the plurality of suction ports can be used to attract and adhere to an interior wall of a stomach such that two stomach portions are formed. Further, the plurality of retractable needles can be used to puncture an interior wall of a stomach by extending through the plurality of openings.

In yet another embodiment, the plurality of retractable needles comprise hollow needles and are capable of applying an adhesive to a tissue. In one embodiment, the plurality of retractable needles can be used to pierce a stomach wall such that the adhesive is applied to the exterior wall of the stomach. In certain embodiments, a first magnetic adhesive comprising a first polarity and a second magnetic adhesive comprising an opposite polarity can be applied to the external walls of the stomach through the retractable needles. In one embodiment, the first magnetic adhesive can be applied to the exterior of the posterior wall of the stomach and the second magnetic adhesive can be applied to the anterior wall of the stomach. In this manner, the attractive magnetic force between the adhesive particles functions to pull the two walls of the stomach together and thereby maintain and stabilize the division between two stomach portions. In certain other embodiments, an additional adhesive may be delivered through the probe to the interior of the stomach to form a continuous seal between the anterior and posterior walls of the stomach such that the two portions of the stomach do not communicate.

In another embodiment, a system and method is provided for using the devices disclosed herein to reduce the medically effective volume of a stomach. One embodiment of the system comprises a device for restricting the capacity of a stomach and a balloon. The balloon is capable of being endoscopically delivered to the stomach and of inflating to a predetermined size. In some embodiments, the balloon serves as a model for the desired volume of the first stomach portion. In yet another embodiment, a method is provided for endoscopically placing the device and balloon into a stomach, suctioning the anterior and posterior walls of the stomach together to form a first stomach portion and a second stomach portion, puncturing the stomach walls to deliver a magnetic adhesive to the exterior of the anterior and posterior stomach walls; and sealing the interior junction between the anterior and posterior stomach walls to ensure minimal communication between the first stomach portion and the second stomach portion.

BRIEF DESCRIPTION OF THE DRAWINGS

FIG. 4 shows a flow chart of one embodiment of a method for using the gastric remodeling device of FIGS. 2A-2D to create a small gastric pouch in a stomach;

DETAILED DESCRIPTION

Figure 1A:
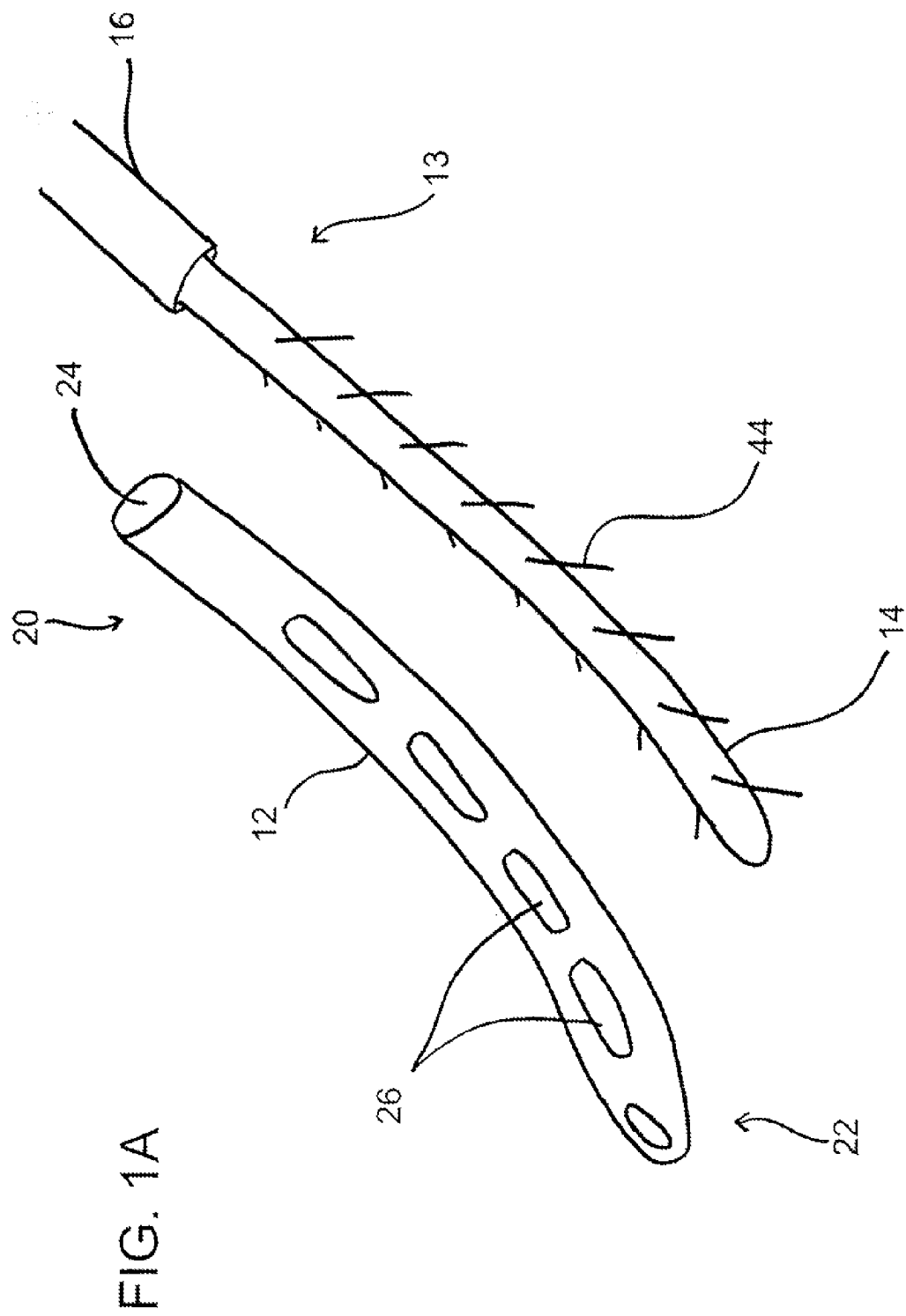
FIG. 1A shows a side view of at least one embodiment of a probe and a shaft of a gastric remodeling device.

Reference will now be made to the embodiments illustrated in the drawings and specific language will be used to describe the same. It will nevertheless be understood that no limitation of scope is intended by the description of these embodiments.

FIGS. 1A-1D show several views of at least one embodiment of a gastric remodeling device 10. In this embodiment, the gastric remodeling device 10 enables a clinician to resize a patient's stomach, while avoiding the nutritional deficiencies observed with Malabsorptive Procedures. Further, the gastric remodeling device 10 does not require sutures or staples that could lead to dehiscence (e.g., the opening of the suture site) or fistula (e.g., an abnormal connection between organs or intestines). Moreover, application of the embodiments of the gastric remodeling device 10 to reduce the medically effective size of a stomach do not produce a significant amount of regurgitation and vomiting, which are commonly observed in connection with conventional methods used to treat obesity.

In the embodiment shown in FIGS. 1A, 1B, 1C, and 1D, the gastric remodeling device 10 is comprised of an esophagogastric malleable probe comprising a first component 12 and a second component 13. The first component 12 of the gastric remodeling device 10 comprises an elongated probe having a proximal end 20, a distal end 22, and an interior 24. The interior 24 of the first component 12 extends throughout the length of the first component 12 and provides a channel through which the distal end 22 of the first component 12 may be accessed when the distal end 22 of the first component 12 is positioned within a body.

Figure 1B:
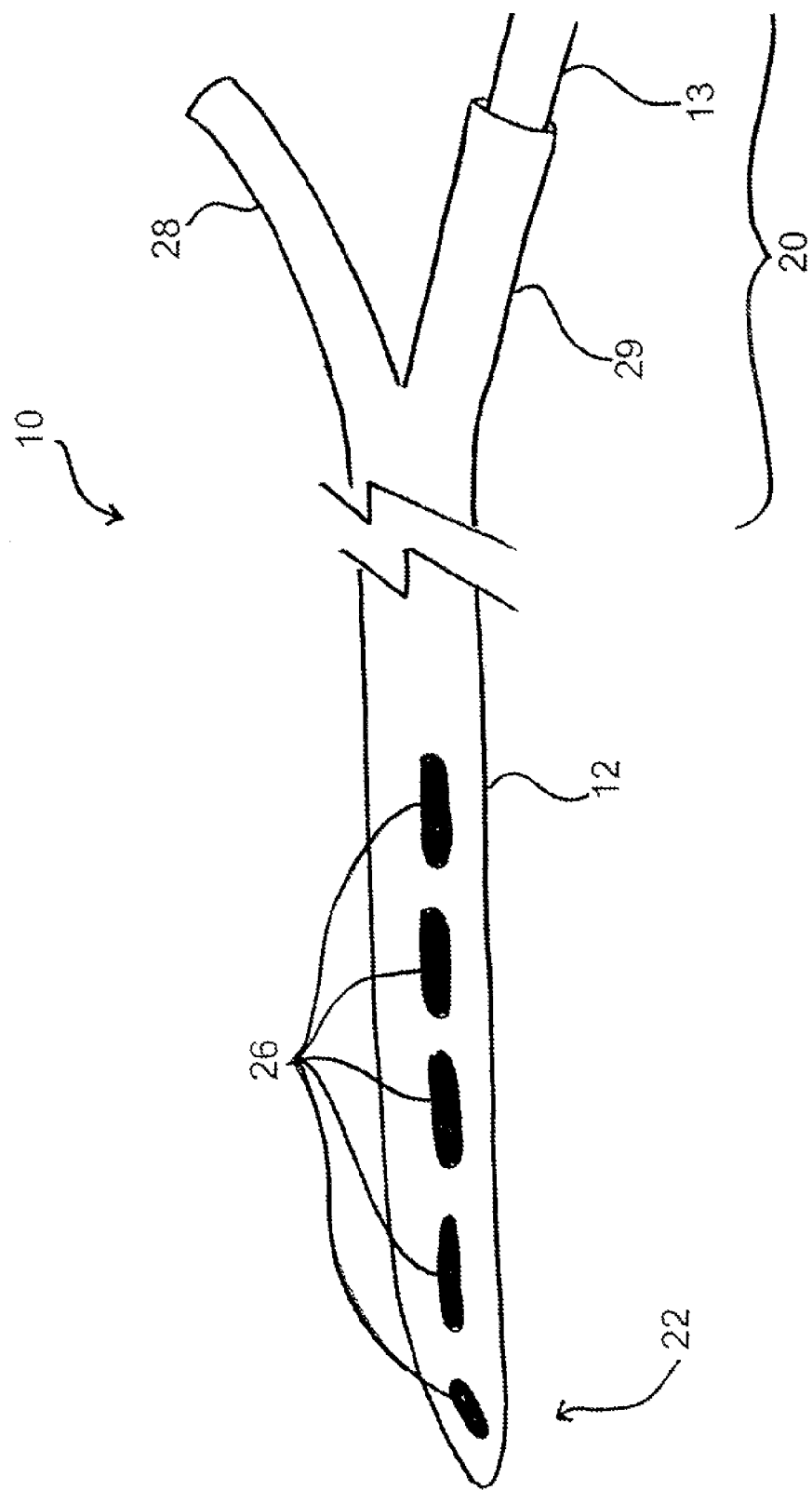
FIG. 1B shows a side view of at least one embodiment of the gastric remodeling device shown FIG. 1A.

As shown in FIG. 1B, the proximal end 20 of the first component 12 comprises a vacuum port 28 and a device port 29. Both the vacuum port 28 and the device port 29 communicate with the interior 24 of the first component 12. For example, when a device is inserted into the device port 29, the device is slidably received by the interior 24 such that the device can be extended to the distal end 22 of the first component 12. Further, when a suctional force is applied by a vacuum source to the vacuum port 28, the force is communicated throughout the interior 24 of the first component 12 and a vacuum is created therein. In one embodiment, a syringe or other vacuum source (not shown) may be coupled with the vacuum port 28 in order to provide appropriate suction throughout the interior 24 of the first component 12. It will be understood that any type of vacuum source may be used to supply suction throughout the interior 24, such as a controlled vacuum system providing specific suction pressures.

The distal end 22 of the first component 12 comprises a plurality of openings 26 disposed thereon. Each of the plurality of openings 26 is in communication with the interior 24 of the first component 12. Further, each of the plurality of openings 26 comprises a configuration capable of attaching to a targeted tissue 75. When a vacuum source is coupled with the vacuum port 28 and an appropriate amount of suctional force is applied, a vacuum is created within the interior 24 of the first component 12, which, in turn, produces an amount of suction through the plurality of openings 26. If sufficient suctional force is provided, the suction within the plurality of openings 26 can effectively pull a targeted tissue 75 into contact with the first component 12 such that a releasable seal is formed therewith. Further, this releasable seal can be maintained for as long as sufficient suctional force is supplied by the vacuum source.

The second component 13 of the gastric remodeling device 10 comprises an elongated shaft 14. The shaft 14 is configured be slidably received by the interior 24 of the first component 12 and comprises a proximal end 40, a distal end 42, an interior, and a plurality of needles 44. The plurality of needles 44 extend from both sides of the shaft 14 and, in at least one embodiment, are concentrated at the distal end 42 thereof. In another embodiment, the location of the needles 44 on the shaft 14 corresponds with the placement of the openings 26 on the first component 12, such that when the distal end 42 of the second component 13 is inserted within the interior 24 of the first component 12, the needles 44 protrude through the openings 26 of the first component 12 (see FIG. 1D).

In at least one embodiment, each of the needles 44 comprises an open tip and a hollow configuration such that a channel 60 is disposed therethrough. The channel 60 is in communication with the interior of the shaft 14 and extends to the open tip of each needle 44 such that a substance can be introduced at the proximal end of the shaft 40, advanced through the interior of the shaft 14, advanced through the channel 60 of the needle 44, and delivered to a targeted tissue through the open tip.

Figure 1C:
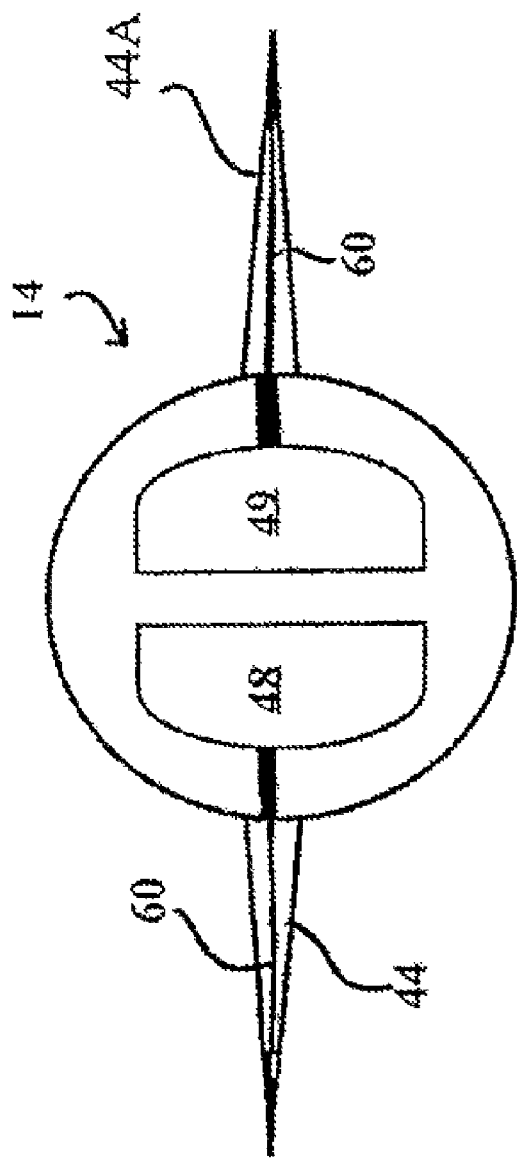
FIG. 1C shows a cross-sectional view of at least one embodiment of the shaft of the gastric remodeling device shown in FIG. 1A.
Figure 1D:
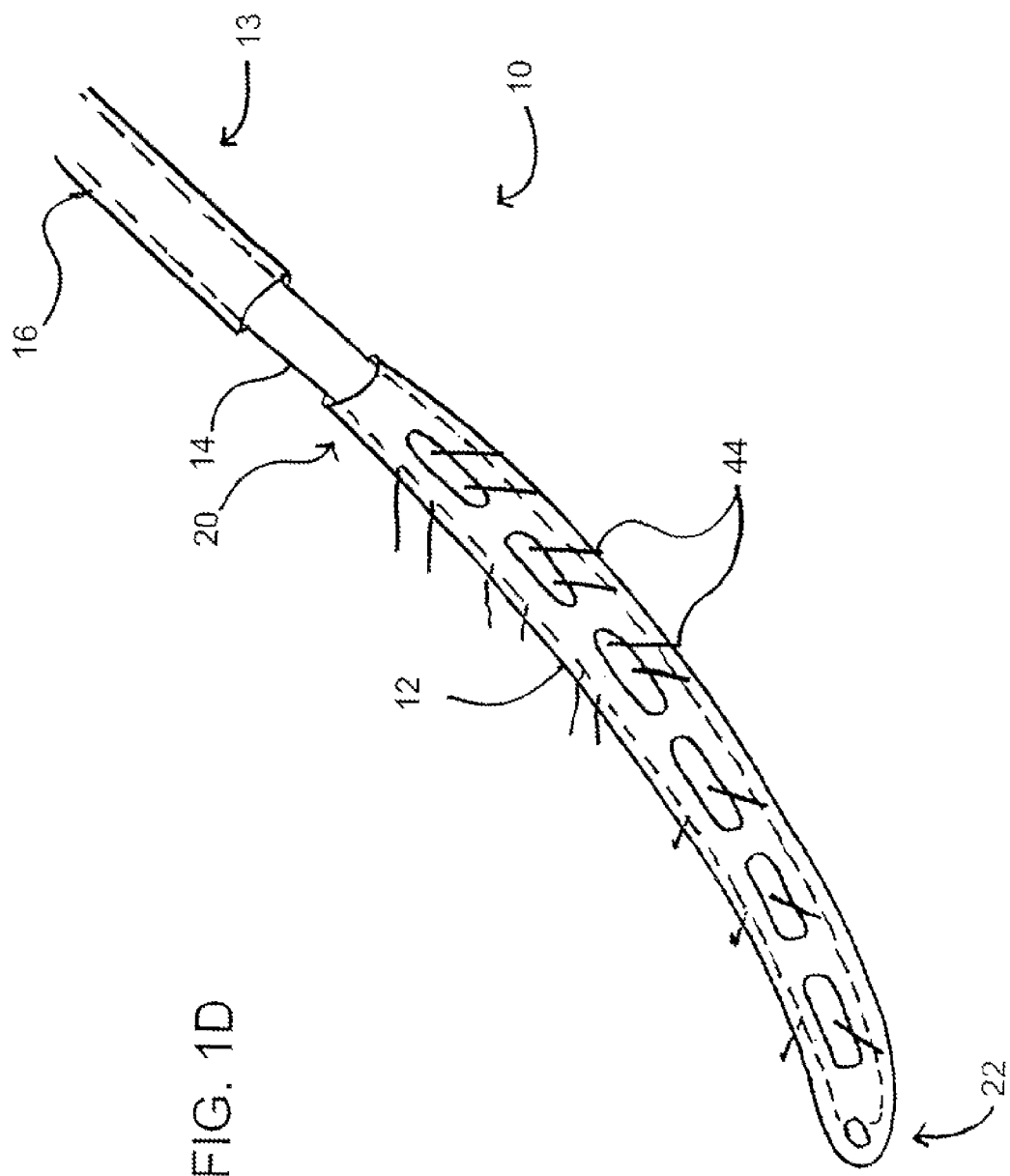
FIG. 1D shows a side view of at least one embodiment of the gastric remodeling device shown in FIG. 1A having a plurality of needles extended therefrom.

In an alternative embodiment shown in FIG. 1C, the interior of the shaft 14 may comprise a first channel 48 and a second channel 49 extending along the length of the shaft 14. In this embodiment, the needles 44 of the first component 12 are also arranged into a first set of needles 44 and a second of needles 44A. In the embodiments shown in FIG. 1C, the first set of needles extends from one side of the shaft 14 and the second set of needles extends from a second side of the shaft 14. Further, the two channels 48, 49 of the shaft 14 are in fluid communication with the hollow interiors of the needles 44 and 44A, respectively. Specifically, the first channel 48 communicates with the channels 60 of the first set of needles 44 and the second channel 49 communicates with the channels 60 of the second set of needles 44A. In this manner, different materials may be inserted through the first and second channels 48, 49 for delivery through the first and second sets of needles 44, respectively.

Accordingly, different materials can be inserted into the first channel 48 and the second channel 49 for delivery to the targeted tissue 75. For example, one substance can be advanced through the first channel 48, through the channels 60 of each of the needles 44 comprising the first set of needles 44, and delivered to the targeted tissue 75 through the open tips of each of those needles 44. Likewise, the same steps can be repeated with a second substance using the second channel 49 and the channels 60 of the second set of needles 44A. In this manner, a clinician may use the independent first and second channels 48, 49 to deliver different substances to the targeted tissue without combining the substances. In one embodiment, a magnetic glue having a first polarity may be delivered through the first channel 48, while a magnetic glue having an opposite polarity can be concurrently delivered through the second channel 49. As the two channels 48, 49 are independent, the two polarities of glue can be separately applied to the targeted tissue through the same shaft 14.

While in one embodiment the first and second channels 48, 49 extend from the proximal end 40 of the shaft 14 to the distal end 42 of the shaft 14, it will be understood that the channels 48, 49 may comprise any length and, furthermore, need not be similarly configured. For example, in one embodiment, the first channel 48 extends into the distal end 42 of the shaft 14, whereas the second channel 49 only extends partially throughout the length of the shaft 14. Additionally, while the first channel 48 and the second channel 49 are shown in FIG. 1C, it will be appreciated that the interior of the shaft 14 may comprise any number of channels extending therethrough.

Each of the plurality of needles 44 is capable of moving between a first resting position and a second retracted position when a force is applied. When no force is applied to the plurality of needles 44 (i.e. the needles 44 are in a resting state), the plurality of needles 44 are positioned in the first resting position. Each of the plurality of needles 44 can be moved into the second retracted position by applying a force. As each of the plurality of needles 44 are biased towards the first resting position, when force is no longer applied, the plurality of needles 44 automatically return to the first resting position.

In one embodiment, when the needles 44 are in the first resting position, the needles 44 are substantially perpendicular to the shaft 14. Further, when the plurality of needles 44 are moved to the second retracted position, the needles 44 are substantially parallel to the shaft 14 and, in one embodiment, lay flat thereon. In another embodiment, when the needles 44 are in the first resting position, each of the needles 44 form about a 45° angle with the shaft 14 (see FIG. 1A). In yet another embodiment, when the plurality of needles 44 are in the first resting position, each of the needles 44 form less than a 90° angle with the shaft 14 and extend away from the proximal end 40 of the shaft 14.

As shown in FIGS. 1A and 1C, the second component 13 may further comprise a sheath 16 having a tubular body, at least one open end, and a lumen. The lumen of the sheath 16 is configured to slidably receive the shaft 14 therein. Further, the sheath 16 is configured to be slidably received by the interior 24 of the first component 12, such that when the sheath 16 is received therein, the plurality of openings 26 of the first component 12 can still communicate with the interior 24 of the first component 12. In other words, the diameter of the sheath 16 is less than the diameter of the interior 24.

When the sheath 16 is applied over the shaft 14, the sheath 16 supplies the requisite force to transition the plurality of needles 44 of the shaft 14 from the first resting position to the second retracted position. In this manner, when the sheath 16 is applied over the shaft 14, the plurality of needles 44 lay in the second retracted position within the lumen of the sheath 16. Further, when the sheath 16 is slidably removed from the shaft 14, the plurality of needles 44 return to the first resting position.

Now referring to FIGS. 2A-2D, at least one embodiment of a gastric remodeling device 100 is shown. Unlike the gastric remodeling device 10 previously described, the gastric remodeling device 100 comprises a first component 112 having a double-lumen probe.

The gastric remodeling device 100 comprises a proximal end 120, a distal end 122, a first component 112, and the second component 13. It will be understood that the second component 13 of the gastric remodeling device 100 is identical to the second component 113 of the gastric remodeling device 10 described in conjunction with FIGS. 1A-1D. Accordingly, the configuration of the second component 13 will not be described in detail with respect to the gastric remodeling device 100, and like reference numerals between FIGS. 1A-1D and FIGS. 2A-2D will refer to like components.

Figure 2A:
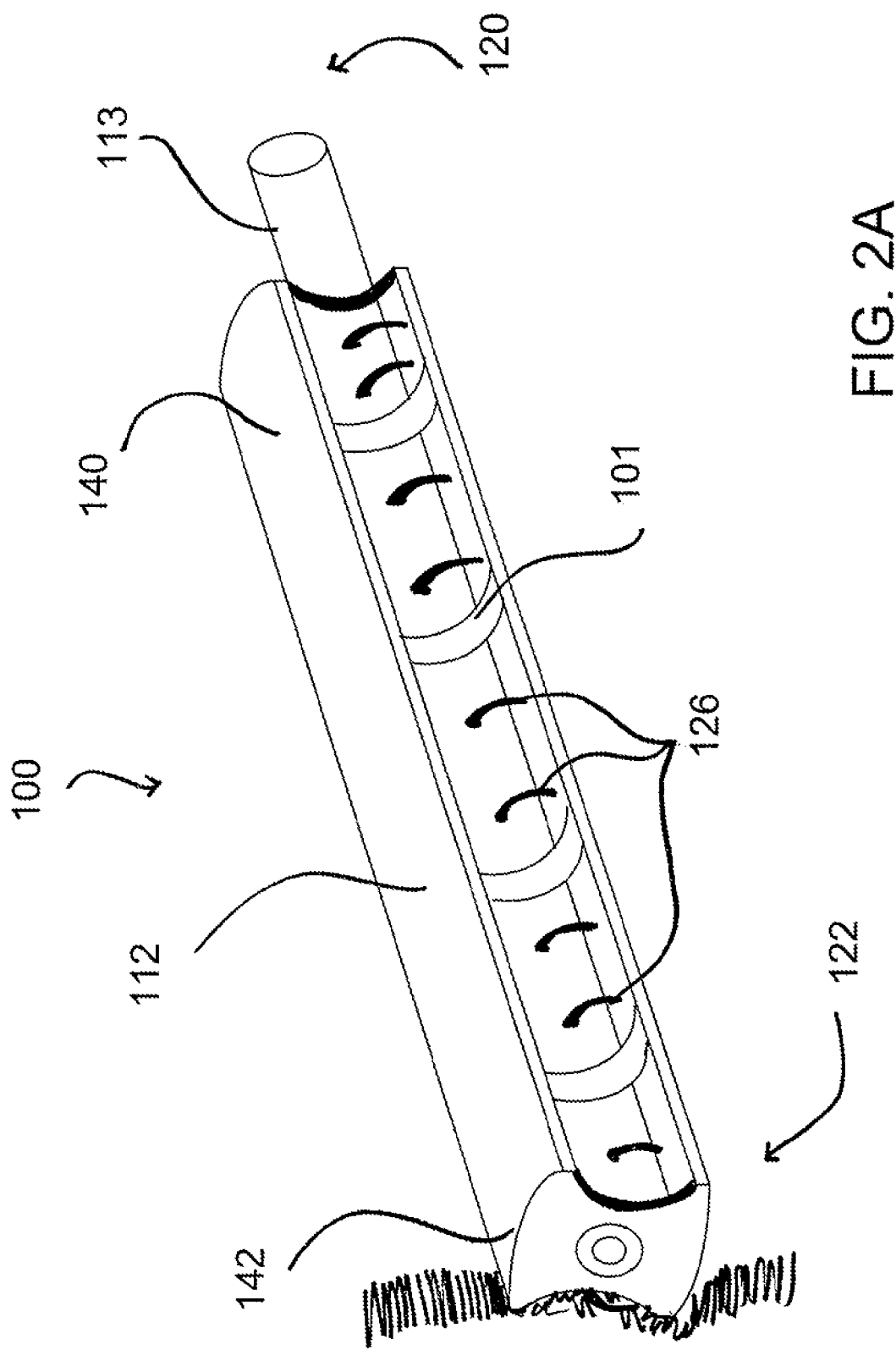
FIG. 2A shows a perspective view of at least one embodiment of a gastric remodeling device.
Figure 2B:
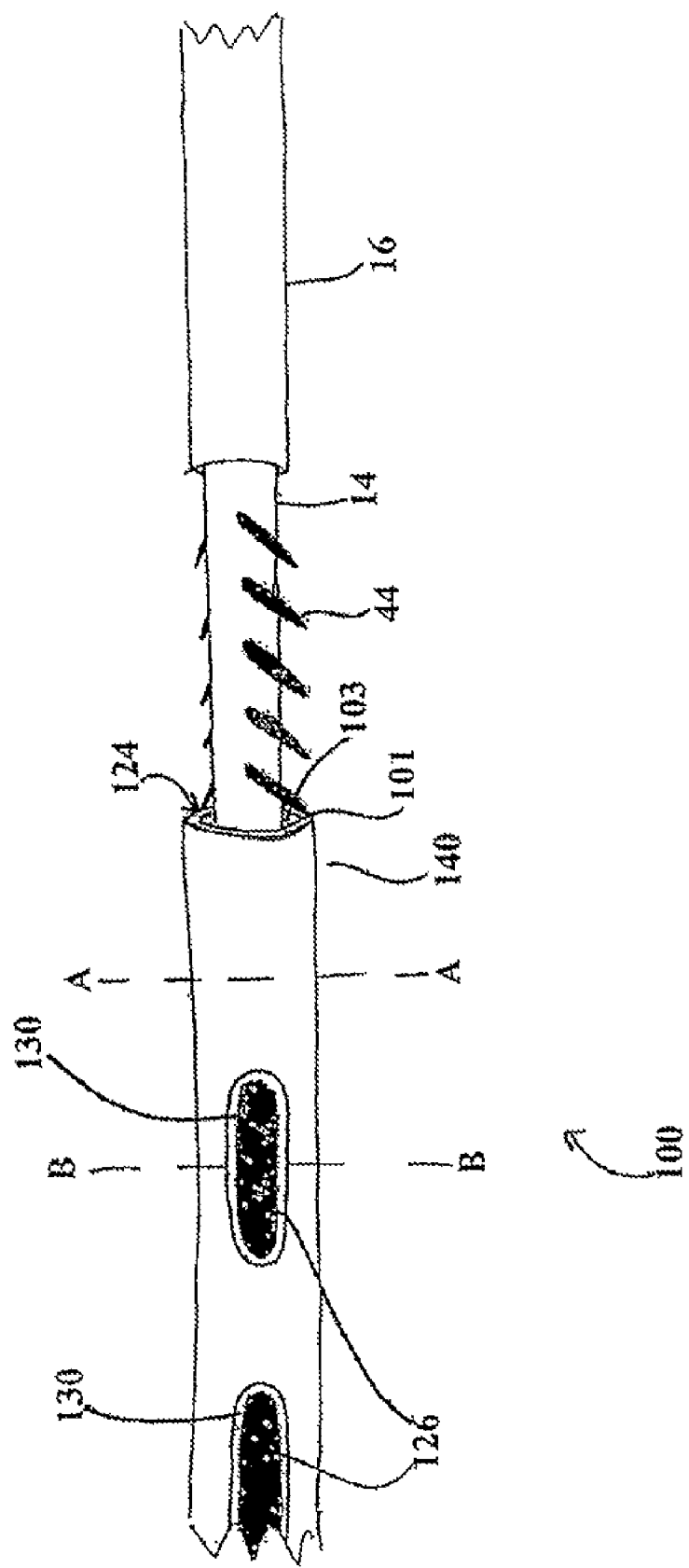
FIG. 2B shows a side view of one embodiment of the components of the gastric remodeling device shown in FIG. 2A.

As shown in FIGS. 2A and 2B, the first component 112 comprises an elongated double-lumen probe having a first end 140, a second end 142, an interior 124, a plurality of openings 126, and a plurality of suction ports 130. The interior 124 of the first component 112 is divided into two cavities: a vacuum channel 101 and a lumen 103. Both the vacuum channel 101 and the lumen 103 each define an interior space. The vacuum channel 101 is for suction and infusion, and the lumen 103 is for slidably receiving the second component 113. The sizes of the vacuum channel 101 and the lumen 103 can vary depending on the specific application for which the gastric remodeling device 100 is used.

Figure 2D:
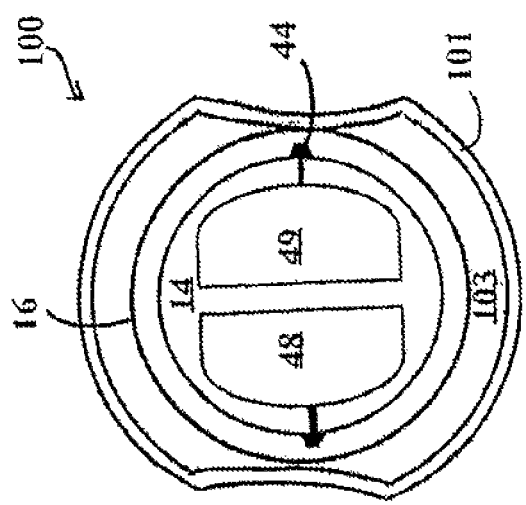
FIG. 2D shows a cross-sectional view of the gastric remodeling device of FIG. 2B taken along axis A-A.
Figure 2C:
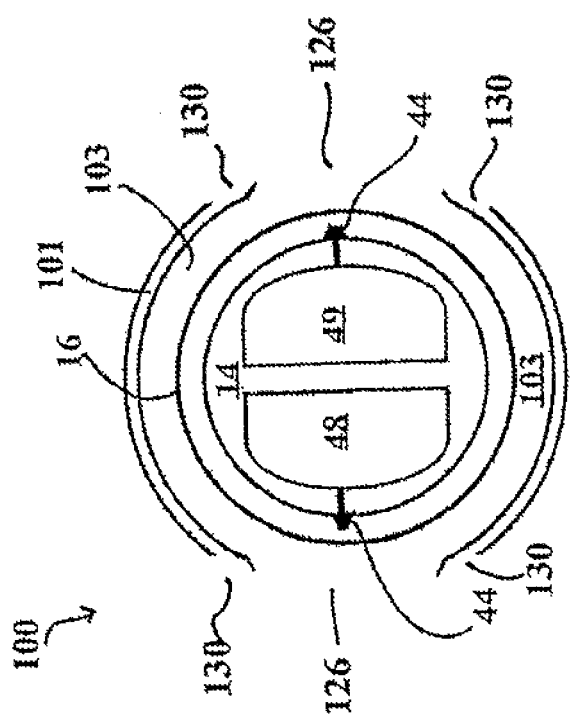
FIG. 2C shows a cross-sectional view of the gastric remodeling device of FIG. 2B taken along axis B-B.

As shown in FIGS. 2C and 2D, the vacuum channel 101 is disposed around the circumference of the first component 112 and the lumen 103 is disposed within the interior 124 of the first component 112. In this manner, the lumen 103 is wholly surrounded by the vacuum channel 101. It will be appreciated that the vacuum channel 101 and the lumen 103 may be disposed in any fashion within the interior 124 of the first component 112 so long as the vacuum channel 101 communicates with the plurality of suction ports 130 of the first component 112. For example, although the vacuum channel 101 and the lumen 103 are shown in FIG. 2A as extending from the first end 140 of the first component 112 along a substantial portion of the length of the first component 112, the vacuum channel 101 and the lumen 103 may or may not span the entire length of the first component 112. Particularly, in at least one embodiment, the vacuum channel 101 does not extend to the second end 142 of the first component 112 to ensure that the suction may be distributed relatively evenly around the circumference of the first component 112 through a plurality of suction ports 130 (as is further discussed below).

The lumen 103 is capable of slidably receiving the second component 13 through the first end 140 of the first component 112, and is further in communication with a plurality of openings 126 disposed on the second end 142 of the first component 112. As such, the plurality of needles 44 of the second component 13 may extend through the plurality of openings 126 when the second component 13 is inserted into the lumen 103 and the shaft 16 is withdrawn.

The vacuum channel 101 is capable of operative connection with a vacuum source at the first end 140 of the first component 112. In one embodiment, when a vacuum source is applied to the vacuum channel 101 at the first end 140, the suctional force is communicated throughout the vacuum channel 101 along the length of the first component 112 and a vacuum is created therein. A syringe or other vacuum source (not shown) may be coupled with the vacuum channel 101 of the first component 112. It will be understood that any type of vacuum source may be used to supply suction throughout the vacuum channel 101, such as a controlled vacuum system providing specific suction pressures. At the second end 142 of the first component 112, a plurality of suction ports 130 are in communication with the vacuum channel 101 for contacting a targeted tissue 75. Each of the plurality of suction ports 130 may comprise any configuration that is capable of attaching to the targeted tissue 75 such that a reversible seal with the targeted tissue 75 is formed when the vacuum source is activated and coupled with the vacuum channel 101.

In clinical application, the gastric remodeling devices 10, 100 may be used to non-surgically and reversibly adjust the medically effective volume of a stomach 77. Specifically, the gastric remodeling devices 10, 100 may be employed to form a small gastric pouch 150 that extends from the gastroesophageal junction ("GEJ") 80 to the duodenum 82 (see FIG. 3A). Further, the gastric remodeling device 10, 100 may be applied such that a gastric evacuation channel is further formed adjacent to the duodenum 82. The small gastric pouch 150 comprises an inlet at the GEJ and an outlet at the duodenum 82, which are the customary entrance for food and fluid entering the stomach 77 and the customary exit for digested food and fluid leaving the stomach 77, respectively. Therefore, even with the gastric remodeling device 10, 100 restricting the medically effective volume of the stomach 77, food digestion occurs through the normal digestive process, thereby avoiding any interruption in the absorption of vitamins and electrolytes typically resulting from Malabsorptive Procedures.

In one embodiment, the gastric remodeling device 100 is used in conjunction with a balloon 50 to form the small gastric pouch 150. The balloon 50 can be any mannequin balloon known in the art as long as the balloon 50 can be introduced endoscopically and the volume of the balloon 50 can be modified when the balloon 50 is positioned within a stomach. When used in conjunction with the gastric remodeling device 10, 100, the balloon 50 serves as a model for the volume of the small gastric pouch 150 that is desired. In other words, the balloon 50 provides a reference point for the clinician with respect to the desired size of the effective volume of the stomach, thereby facilitating accuracy and increasing the overall speed of the procedure. While the application of the gastric remodeling device 10, 100 is described in conjunction with a balloon 50 to facilitate the proper sizing of the effective volume, it will be appreciated that the gastric remodeling device 10, 100 can be delivered to the stomach without the use of a balloon 50 or other modeling device. Furthermore, the gastric remodeling device 10, 100 can be used in conjunction with any other modeling device known in the art, so long as the modeling device is capable of endoscopic insertion.

Now referring to FIG. 4, a flow chart is shown of a method 300 for using the gastric remodeling device 100 to reduce the effective size of a stomach. For ease of understanding, the steps of the related methods described herein will be discussed relative to components of the gastric remodeling device 100 shown in FIGS. 2A-2D, but it will be appreciated by one skilled in the art that any such system or device can be used to perform these methods, including without limitation the gastric remodeling device 10, so long as the device has a probe, a shaft that is slidably moveable with respect to the probe, a plurality of needles, and a plurality of vacuum ports for attaching to a targeted tissue.

Figure 3A:
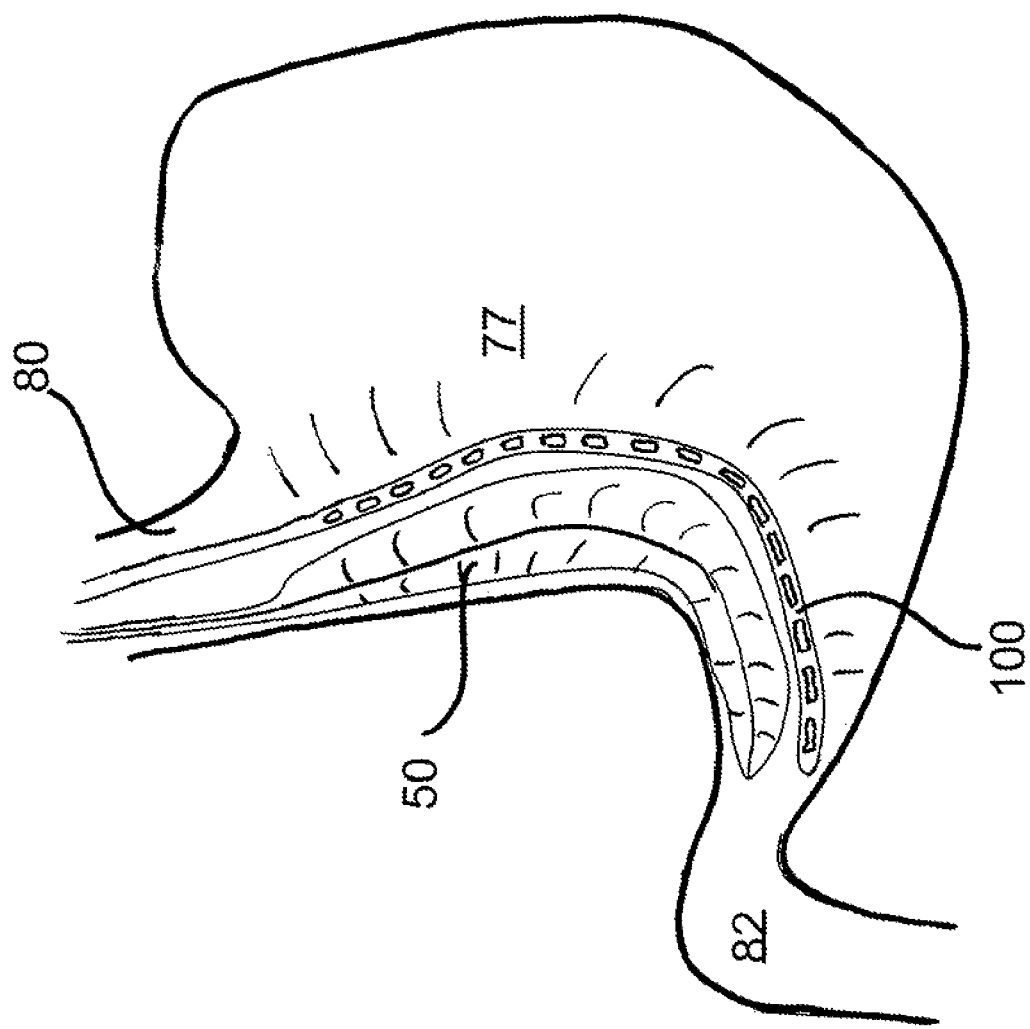
FIG. 3A shows a side view of a system comprising at least one embodiment of the gastric remodeling device of FIGS. 1A-1D and a balloon positioned within a stomach.

At step 202, the balloon 50 is introduced into a stomach 77 endoscopically under fluoroscopic control. In one embodiment, the balloon 50 is positioned adjacent to the lesser curvature of the stomach, as shown in FIG. 3A. Once the balloon 50 is properly positioned within the stomach, the balloon 50 is inflated to the desired size through a tube or other means commonly known in the art. At step 204, the gastric remodeling device 100 is endoscopically introduced into the stomach of the patient. Prior to inserting the gastric remodeling device 100 into the patient, the sheath 16 of the second component 13 is applied over the shaft 14 and the second component 13 is slidably engaged with the interior 124 of the first component 112. As such, the plurality of needles 44 of the shaft 14 are not exposed when the gastric remodeling device 100 is endoscopically introduced. After the components of the gastric remodeling device 100 are properly configured, the distal end of the gastric remodeling device 10 is delivered to the stomach 77 endoscopically under fluoroscopic control.

Figure 3B:
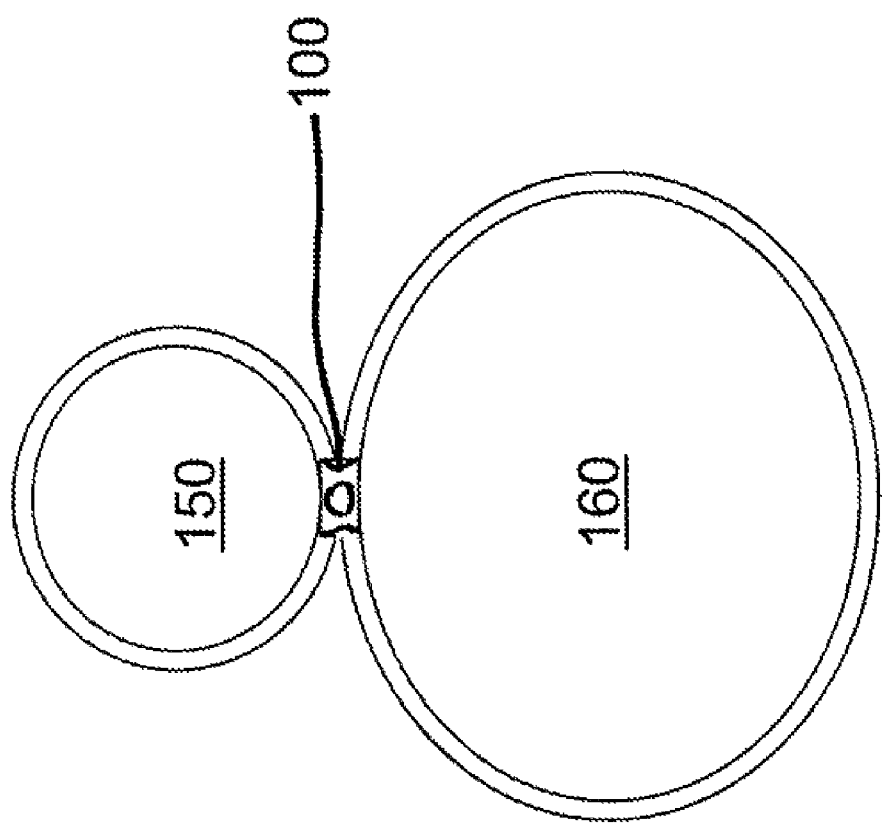
FIG. 3B shows a top, cross-sectional view of the system shown in FIG. 3A positioned within a stomach.
Figure 5A:
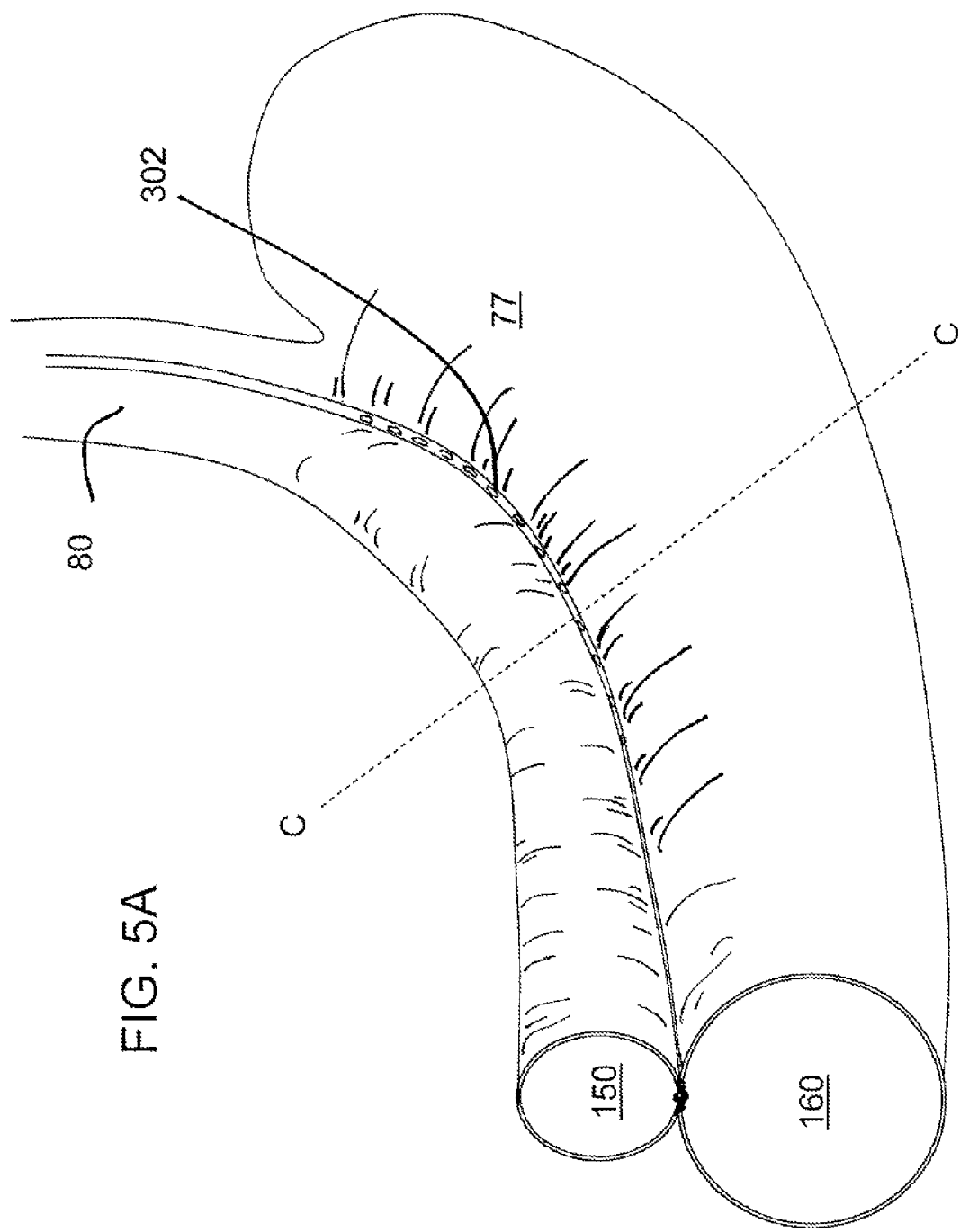
FIG. 5A shows a perspective view of the outside of a stomach that has been divided into a first stomach portion and a second stomach portion by at least one embodiment of the gastric remodeling device of FIGS. 2A-2D.
Figure 5B:
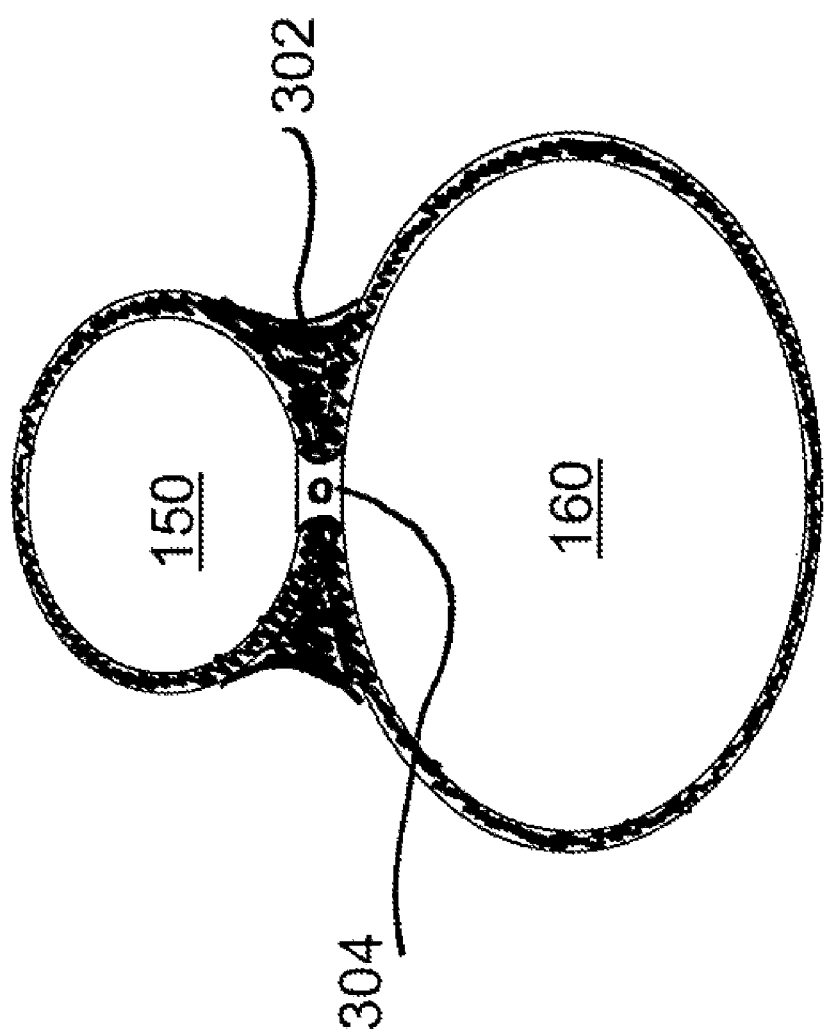
FIG. 5B shows a cross-sectional view of the stomach of FIG. 5A taken along axis C-C.

In one embodiment, the gastric remodeling device 100 is positioned immediately adjacent to the balloon 50 and situated such that the plurality of openings 126 on each side of the first component 112 are adjacent to the anterior and posterior walls of the stomach 77. After the gastric remodeling device 100 is positioned in the desired location within the stomach 77, at step 206 the gastric remodeling device 100 engages the interior stomach walls using a suctional force. Specifically, a vacuum source is coupled with vacuum channel 101 and used to supply suction therethrough along the length of the first component 112. In this manner, a suctional force is exerted through the plurality of suction ports 130, which pulls the anterior and posterior walls of the stomach 77 into contact with the first component 112. As, in this embodiment, the gastric remodeling device 100 is positioned immediately adjacent to the balloon 50, the suction effectively wraps the walls of the stomach 77 around the balloon 50. Further, the stomach walls are held in place around the balloon 50 for as long as the suction is supplied through the vacuum channel 101 of the first component 112. As shown in FIGS. 3A and 3B, the stomach is now divided into two sections, a small gastric pouch 150 having a volume substantially equal to the volume of the inflated balloon 50 contained therein, and a residual gastric chamber 160 that is bypassed in digestive functions.

With the walls of the stomach 77 securely coupled to the gastric remodeling device 100, at step 208 the balloon 50 may optionally be deflated and removed through the esophagus 80. Alternatively, the method 300 may proceed directly from step 206 to step 210 and withdraw the balloon 50 at some later point in the procedure. At step 210, the sheath 16 is withdrawn through the proximal end 120 of the first component 112, thereby deploying the plurality of needles 44 against the portions of the interior stomach wall that are suctioned against the gastric remodeling device 100. Specifically, when the sheath 16 is slidably removed from the shaft 14, there is no longer a force holding the plurality of needles 44 in the second retracted position. Accordingly, as previously described, each of the needles 44 automatically shifts from the second retracted position to the first resting position. The plurality of needles 44 aligned with the plurality of openings 126 extend through the plurality of openings 126, thereby puncturing the interior anterior and posterior walls of the stomach suctioned thereto. In one embodiment, the plurality of needles 44 completely puncture the stomach walls such that the open tips of the needles 44 clear the exterior wall of the stomach 77.

In one embodiment, the shaft 14 may be slightly advanced or withdrawn within the first component 112 of the gastric remodeling device 100 to facilitate the complete puncture of the stomach walls. Fluoroscopic vision may further be utilized at step 210 to assist in controlling the penetration of the plurality of needles 44 through the walls of the stomach 77. Further, in at least one embodiment, the vacuum source increases the amount of suctional force supplied at step 210 in order to ensure that an adequate amount of pressure is maintained between the plurality of needles 44 and the interior walls of the stomach when the plurality of needles 44 are deployed.

After the plurality of needles 44 successfully puncture the stomach walls, an adhesive is advanced through the interior of the shaft, the channels 60 of the needles 44, and onto the exterior of the stomach 77 at step 212. The adhesive may comprise any micromagnetic adhesive known in the art, including without limitation, microbeads, magnetic liposomes, or other magnetic glue beads. In the embodiment of the interior of the shaft 14 of the gastric remodeling device 100 comprises a first channel 48 and a second channel 49 and the shaft comprises a first and second set of needles 44, the first and second channels 48, 49 may be employed to prevent magnetic adhesives comprising opposite polarities from mixing. Specifically, in this embodiment, a magnetic adhesive comprising a first polarity is injected into the first channel 48 and advanced through the proximal end of the shaft 14, the channels 60 of the first set of needles 44, and out of the open tips of the needles 44. In this manner, the magnetic adhesive comprising a first polarity is applied to the posterior exterior surface of the stomach 77. Concurrently or thereafter, a magnetic adhesive comprising an opposite polarity is applied to the anterior exterior surface of the stomach 77 in the same manner: the magnetic adhesive comprising the opposite polarity is injected into the second channel 49 and advanced through the proximal end of the shaft 14, the channels 60 of the second set of needles 44, and out of the open tips of the needles 44.

As the two sets of needles 44 are positioned on opposite sides of the stomach (through both the anterior and posterior walls), the two exterior stomach surfaces are coated with attracting particles or attracting magnetic liposomes. In this manner, a magnetic force is generated that provides a sandwiching effect on the stomach wall, thereby forcing the collapse of the stomach 77 along the line of adhesive application. Further, the magnetic force is sufficient to hold the stomach walls together without the assistance of the gastric remodeling device 100. Accordingly, at step 212, the suction provided through the vacuum channel 101 of the first component 112 is no longer required to maintain the division between the small gastric pouch 150 and the residual gastric chamber 160.

At step 214, the suctional force provided by the vacuum source through the vacuum channel 101 is ceased and the gastric remodeling device 100 is slowly withdrawn under fluoroscopic control. In the event the balloon 50 has not yet been withdrawn from the stomach 77, the balloon 50 is also withdrawn at this step. As the gastric remodeling device 100 is withdrawn, a second adhesive is delivered to the interior walls of the stomach 77 adjacent to where the posterior wall and the anterior walls meet. Specifically, the second adhesive may be injected to the interior 124 of the first component 112 and applied to the tissue through the plurality of openings 126 in the first component 112. Alternatively or concurrently, the second adhesive may be injected into the vacuum channel 101 and applied to the tissue through the plurality of suction ports 130. In this manner, a seal is formed on the interior of the stomach 77 between the anterior and posterior gastric walls that held together by the magnetic force generated by the magnetic adhesive applied to the exterior of the stomach walls. After a sufficient amount of time has passed to allow the adhesive to form a seal within the interior of the stomach, a radioscopic control may be performed to corroborate the gastric pouch size (i.e. the size of the first stomach section 70), the sealing continuity, and to identify any possible leaks that may exist.

Using the gastric remodeling devices 10, 100 described herein in the treatment of obesity avoids the nutritional deficiencies observed after Malabsorptive Procedures, does not require sutures or staples which may lead to dehiscence or fistula formation, or produce the degree of regurgitation and vomiting observed in connection with conventional methods. Moreover, each of the devices described herein may be inserted into the body cavity endoscopically, thereby decreasing the stress associated with the procedure and the patient's recovery time. It will be recognized by one of skill in the art that any of the devices described herein may be employed in combination with the other conventional bariatric procedures.

While various embodiments of devices, systems, and methods for restricting the medically effective size of a stomach have been described in considerable detail herein, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. An apparatus for restricting the medically effective volume of a stomach, comprising:
   a probe configured for placement between walls of a stomach, the probe comprising an exterior wall, at least one lumen within said exterior wall, and a plurality of openings through the exterior wall that are in communication with the at least one lumen;
   a vacuum source operatively coupled with the at least one lumen of the probe and capable of providing suction through the plurality of openings; and
   a slidable member positioned within the at least one lumen of the probe, the slidable member comprising a plurality of retractable needles that are moveable between a retracted position and an extended position and said member configured to be slidably positioned within the at least one lumen of the probe;

wherein operation of the vacuum source causes the releasable coupling of the walls of the stomach with the exterior of the probe, thereby creating a first stomach portion and second stomach portion, and the plurality of retractable needles are capable of moving to the extended position, extending through the plurality of openings, and puncturing the walls of the stomach when the walls of the stomach are releasably coupled with the exterior of the probe.

2. The apparatus of claim 1, wherein the first stomach portion is for primary digestion of ingested food.

3. The apparatus of claim 1, wherein the slidable member further comprises:
a sheath comprising a hollow interior and configured to be slidably received within the at least one lumen of the probe; and
a shaft positioned within the hollow interior of the sheath and configured to be slidably moveable therein, the shaft comprising a hollow interior, an exterior surface, and the plurality of retractable needles attached to said exterior surface:
wherein the plurality retractable needles are coupled with the exterior surface of the shaft and each of the plurality of retractable needles further comprises an open tip and a lumen, the lumen communicating between the interior of the shall and the open tip of the retractable needle.

4. The apparatus of claim 1, wherein the probe is configured to be endoscopoically delivered into a stomach.

5. The apparatus of claim 3, wherein the extended position of each of the plurality of retractable needles comprises a resting position and the retracted position of each of the plurality of retractable needles comprises a biased position.

6. The apparatus of claim 3, wherein when the plurality of retractable needles are in the first extended position, the plurality of retractable needles extend from the shaft at about a ninety degree angle.

7. The apparatus of claim 3, wherein when the plurality of retractable needles are in the second retracted position, the plurality of retractable needles are substantially parallel to the shaft.

8. The apparatus of claim 3, wherein when the plurality of retractable needles are in the extended position, the plurality of retractable needles form between about a thirty degree angle and about a ninety degree angle with the shaft.

9. The apparatus of claim 1, wherein the vacuum source comprises a syringe.

10. The apparatus of claim 3, wherein when the shaft is positioned within the interior the sheath, the plurality of retractable needles are in the retracted position.

11. The apparatus of claim 3, wherein when the sheath is slidably removed from the interior of the shaft, the plurality of retractable needles move into the extended position.

12. The apparatus of claim 3, wherein the probe further comprises:
a first lumen,
a second lumen,
a vacuum port operatively connected with the vacuum source and the first lumen of the probe, and
a device port operatively coupled with the second lumen or the probe and capable of slidably receiving the sheath therein.

13. The apparatus of claim 12, wherein the first lumen of the probe comprises a vacuum channel and the second lumen of the probe is in communication with the plurality of openings through the exterior wall of the probe.

14. The apparatus of claim 13, wherein the exterior wall of the probe further comprises a plurality of suction ports, each of the plurality of suction ports operatively coupled with the vacuum source through the vacuum channel of the probe.

15. The apparatus of claim 3, wherein
the interior of the shaft further comprises a first channel and a second channel, and
the plurality of retractable needles further comprise a first set of retractable needles and a second set of retractable needles, the first set of retractable needles extending from a first side of the shall and the second set of retractable needles extending from the second side of the shaft; and
wherein the lumens of each of the retractable needles of the first set of retractable needles are operatively connected to the first channel and the lumens of each of the retractable needles of the second set of retractable needles are operatively connected to the second channel.

16. The apparatus of claim 1, wherein the plurality of retractable needles further comprise a first set of retractable needles and a second set of retractable needles, the first set of retractable needles extending from a first side of the slidable member and the second set of retractable needles extending from a second side of the slidable member.

17. The apparatus of claim 3, wherein removal of the sheath from the at least one lumen of the probe causes the plurality of retractable needles to shift from the retracted position to the extended position.

18. The apparatus of claim 15, further comprising a first magnetic adhesive for application to an exterior portion of the stomach, wherein the open tip of each of the plurality of retractable needles is capable of delivering the first magnetic adhesive to the exterior portion of the stomach.

19. The apparatus of claim 18, wherein the first magnetic adhesive comprises magnetic glue beads.

20. The apparatus of claim 19, wherein the magnetic glue beads comprise magnetic liposomes.

21. The apparatus of claim 19, further comprising a second adhesive for application to an interior portion of the walls of the stomach, wherein the plurality of openings of the probe are capable of delivering the second adhesive to the interior portion of the walls of the stomach.

22. The apparatus of claim 14, further comprising:
a first magnetic adhesive for application to an exterior portion of the stomach; and a second adhesive for application to an interior portion of the walls of the stomach;
wherein the open tip of each of the plurality of retractable needles is capable of delivering the first magnetic adhesive to the exterior portion of the stomach and the plurality of suction ports are capable of delivering the second adhesive to the interior portion of the walls of the stomach.

23. An apparatus for restricting the medically effective volume of a stomach, comprising:
a probe for placement between walls of a stomach, the probe comprising an exterior wall, at least one lumen within said wall and a plurality of openings through the exterior wall, the plurality of openings communicating with the at least one lumen of the probe,
a vacuum source operatively coupled with the at least one lumen of the probe and capable of providing suction through the plurality of openings in the probe; and
a slidable member positioned within the at least one lumen of the probe and configured to be slidably moveable therewith, the slidable member comprising:
a sheath composing a hollow interior and configured to be slidably received within the at least one lumen of the probe; and a shaft positioned within the interior of the sheath and configured to be slidably moveable within the interior of the sheath, the shaft comprising a hollow interior, an exterior surface, and a plurality of retractable needles;

wherein the plurality of retractable needles are coupled with the exterior surface of the shall and each of the plurality of retractable needles further comprises an open tip and a lumen, the lumen operatively coupled with the interior of the shaft and extending to the open tip of each of the plurality of retractable needles; and wherein operation of the vacuumm source causes the releasable coupling of the walls of the stomach with the exterior wall of the probe, thereby creating the first stomach portion and a second stomach portion, and the plurality of retractable needles are capable of extending through the plurality of openings and puncturing the walls of the stomach when the walls of the stomach are releasably coupled with the exterior of the probe.

24. An apparatus for restricting the medically effective volume of a stomach, comprising:
a flexible probe for placement between the interior walls of a stomach, the flexible probe comprising a lumen and a suction system;
a wall injection device positioned within the lumen of the probe and slidably moveable therewith, the wall injection device comprising a puncturing mechanism and a removable sheath for temporarily enclosing the puncturing mechanism, and
an adhesive delis cry system positioned within the lumen of the probe;
wherein operation of the suction system causes a releasable seal to be formed between the interior walls of the stomach and the flexible probe, thereby creating a first stomach portion and a second stomach portion, operation of the puncturing mechanism causes the interior walls of the stomach to be punctured, and operation of the adhesive delivery system causes at least one adhesive to be delivered to an exterior portion of the walls of the stomach, thereby maintaining the formation of the first stomach portion and the second stomach portion.

25. The apparatus of claim 24, wherein operation of the adhesive delivery system further causes at least one adhesive to be delivered to an interior portion of the walls of the stomach, thereby securing the formation of the first stomach portion and the second stomach portion.

26. A system for restricting the medically effective volume of a stomach, the system comprising:
an inflatable balloon capable of comprising a predetermined volume and configured for endoscopic delivery to a stomach;
a flexible probe for placement adjacent to the inflatable balloon and between the interior walls of a stomach, the flexible probe comprising a lumen and a suction system;
a wall injection device positioned within the lumen of the probe and slidably moveable therewith, the wall injection device comprising a puncturing mechanism and a removable sheath for temporarily enclosing the puncturing mechanism; and
an adhesive delivery system positioned within the lumen of the probe;
wherein operation of the suction system causes a releasable seal to he formed between the interior walls of the stomach and the flexible probe, thereby creating a first stomach portion and a second stomach portion, operation of the puncturing mechanism causes the interior walls of the stomach to be punctured, and operation of the adhesive delivery system causes at least one adhesive to be delivered to an exterior portion of the walls of the stomach and an interior portion of the walls of the stomach, thereby maintaining the formation of the first stomach portion and the second stomach portion.

27. A method for treating obesity, the method comprising the steps of
providing a system for restricting the medically effective volume of a stomach, the system comprising:
an inflatable balloon capable of comprising a predetermined volume and configured for endoscopic delivery to the stomach;
an endoscopic device comprising
a flexible probe for placement between the interior walls of the stomach, the flexible probe comprising a lumen and a suction system,
a wall injection device positioned within the lumen of the probe and slidably moveable therewith, the wall injection device comprising a puncturing mechanism and a removable sheath for temporarily enclosing the puncturing mechanism, and
an adhesive delivery system positioned within the lumen of the probe,
wherein operation of the suction system causes a releasable seal to be formed between the interior walls of the stomach and the flexible probe, thereby creating a first stomach portion and a second stomach portion, operation of the puncturing mechanism causes the interior walls of the stomach to be punctured, and operation of the adhesive delivery system causes at least one adhesive to be delivered to an exterior portion of the walls of the stomach, thereby maintaining the formation of the first stomach portion and the second stomach portion;
introducing the balloon and the endoscopic device into a stomach endoscopically;
inflating the balloon to the predetermined volume;
creating the first stomach portion and the second stomach portion by attracting an anterior wall and a posterior wall of the stomach to the endoscopic device through operation of the suction system;
accessing exterior portions of the anterior wall and the posterior wall through operation of the puncturing mechanism;
securing the anterior wall the posterior wall together through the use of a magnetic adhesive;
deflating and withdrawing the balloon from the stomach; and
withdrawing the endoscopic device from the stomach.

28. The method of claim 27, wherein the operation of the adhesive delivery system further causes at least one adhesive to be delivered to an interior portion of the walls of the stomach, and further comprising the step of delivering a second adhesive to an interior portion of the anterior wall and the posterior wall through operation of the adhesive delivery system, thereby forming a seal between the junction of the anterior wall and the posterior wall.

29. The method of claim 28, further comprising the step of performing a radioscopic control to corroborate the size of the first stomach portion and confirm the continuity of the seal between the anterior wall and the posterior wall.

30. The method of claim 28, further comprising the step of performing a radioscopic control for the detection of leaks in the seal between the junction of the anterior wall and the posterior wall.

31. The method of claim 27, wherein:
the flexible probe for placement between the interior walls of the, stomach further comprises:

an exterior, at least one lumen and a plurality of openings in the exterior, the plurality of openings communicating with the at least one lumen of the probe, and a vacuum source operatively coupled with the at least one lumen of the probe and capable of providing suction through the plurality of openings in the probe, wherein the vacuum source is capable of releasably coupling the walls of the stomach with the exterior of the probe, thereby creating a first stomach portion and a second stomach portion; and the step of creating the first stomach portion and the second stomach portion by attracting an anterior wall and a posterior wall of the stomach to the endoscopic device through operation of the suction system further comprises:

supplying a suctional force through the plurality of openings in the probe by operation of the vacuum source, and applying the suctional force to the interior portions of the anterior and posterior walls of the stomach, thereby creating a releasable seal between the exterior of the probe and the interior portions of the anterior and posterior walls of the stomach.

32. The method of claim 31, wherein
the wall injection device further comprises:
a sheath comprising an interior and configured to be slidably received within the at least one lumen of the probe; and a shaft positioned within the interior of the sheath and configured to be slidably moveable within the interior of the sheath, the shaft comprising an interior, an exterior, and the plurality of retractable needles;

wherein the plurality of retractable needles are coupled with the exterior of the shaft and each of the plurality of retractable needles further comprises an open tip and a lumen, the lumen operatively coupled with the interior of the shaft and extending to the open tip of each of the plurality of retractable needles; and the step of accessing exterior portions of the anterior wall and the posterior wall through operation of the puncturing mechanism further composes the steps of:

exposing the plurality of retractable needles through removal of the sheath from the shaft; and puncturing the anterior wall and the posterior wall with the plurality of retractable needles such that the open tips of the plurality of retractable needles are positioned externally of the stomach.

33. The method of claim 32, further comprising the step of increasing the suctional force through the plurality of openings in the probe by operation of the vacuum source.

34. The method of claim 32, wherein
the adhesive delivery system further comprises the shall and the interior of the shaft further comprises
a first channel and a second channel, the plurality of retractable needles further comprise a first set of retractable needles and a second set of retractable needles, the first set of retractable needles extending from a first side of the shaft and the second set of retractable needles extending from the second side of the shaft, and the lumens of each of the retractable needles of the first set of retractable needles are operatively connected to the first channel and the lumens of each of the retractable needles of the second set of retractable needles are operatively connected to the second channel; and the step of securing the anterior wall and the posterior wall together through the use of a magnetic adhesive further comprises the steps of:

injecting a magnetic adhesive of a first polarity into the first channel of the shaft;

injecting a magnetic adhesive having a second polarity into the second channel of the shaft wherein the second polarity is opposite of the first polarity;

applying the magnetic adhesive having the first polarity to the exterior of the posterior wall of the stomach by advancing the adhesive through the first channel, into the lumens of the first set of retractable needles, and through the open tips of needles of the first set at of retractable needles;

applying the magnetic adhesive having the second polarity to the exterior of the anterior wall of the stomach by advancing the adhesive through the second channel, into the lumens of the second set of retractable needles, and through the open tips of the needles of the second set of retractable needles; and allowing the magnetic force between the magnetic adhesives to hold the interior and posterior walls of the stomach together along the point of adhesive application.

\* \* \* \* \*